Oct. 25, 1938. M. H. HORVATH Plant Pat. 299
ROSE
Filed Sept. 1, 1937
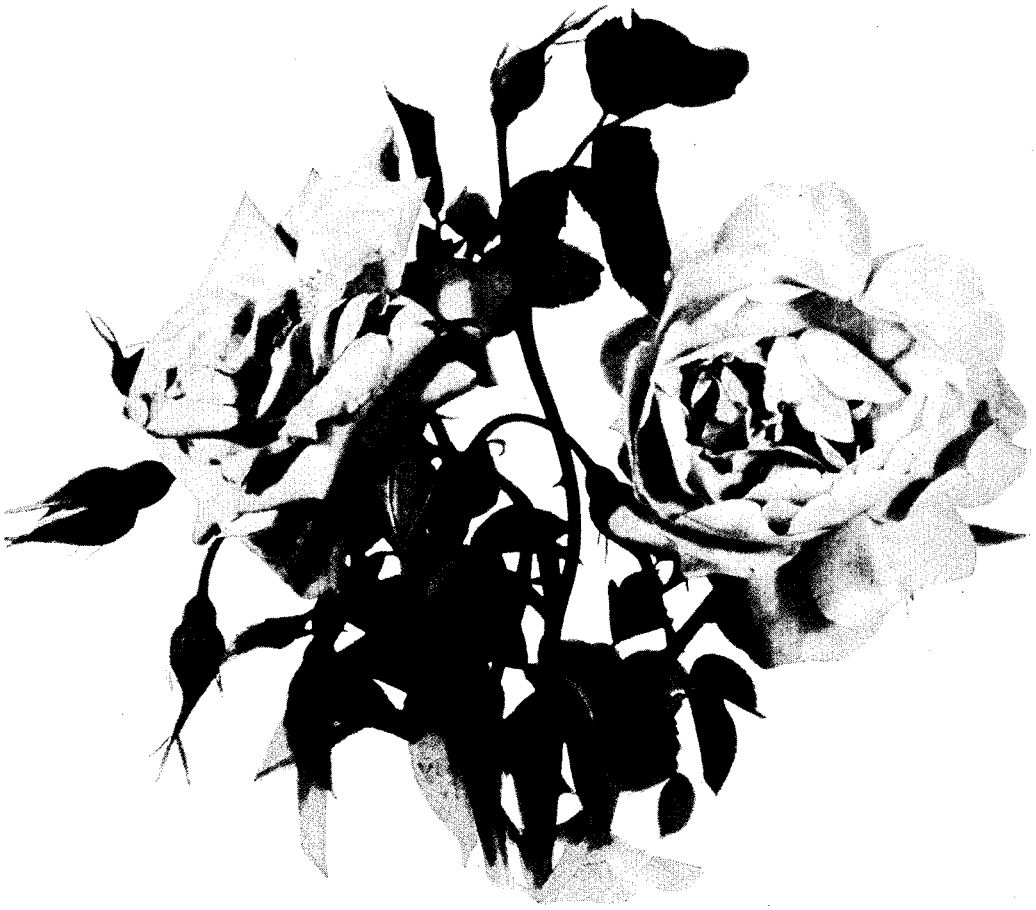
Inventor:
Michael H. Horvath
By John H. Leonard.
Attorney Patented Oct. 25, 1938

Plant Pat. 299

UNITED STATES PATENT OFFICE

299

ROSE

Michael H. Horvath, Mentor, Ohio

Application September 1, 1937, Serial No. 162,066

1 Claim. (Cl. 47—61)

This invention relates to a novel and distinct variety of perpetual flowering rose produced by the intercross of species "*Rosa multiflora*" and species "*Rosa canina*", followed by a re-cross with variety "Horvath's Improved Hortulanus Budde." Successful asexual reproduction has been made.

This new variety is of a very hardy nature, growing without protection in the temperate region to an ultimate height of from twenty-four to thirty inches and with a spread of eighteen inches or greater. It can be successfully grown with protection in the colder regions where the growing of roses has been impossible or exceedingly difficult.

The flowers, of a glowing cherry red color comparable to Maerz and Paul Plate No. 2 L–6, and having a light orange center, comparable to "Golden Glow", Plate No. 9L–6, are vividly brilliant. Augmenting this brilliance is a distinctive reflection of a fiery orange glow which radiates from the flower in its full bloom stage. Each flower has from thirty to thirty-six petals.

The foliage is characteristically healthy and of a glaucous green color, comparable to "Danube Green" Plate No. 31 A–10, the pedicels and stalks are of a like color.

The rose blooms profusely, singly and in clusters, throughout the entire summer season, making the variety especially adapted for giving lasting sweeps of brilliant color.

The drawing further illustrates many of the characteristics which are not found in the parent stock or in other rose varieties and which make the variety of more value as a shrub and increase its attractiveness.

The following is a detailed description of my new variety:

Parentage:

*Seedling.*—Seed parent—*Rosa multiflora* x *Rosa canina.* Pollen parent—Improved Horvath's Hortulanus Budde.

Classification:

*Botanic and commercial.*—Canina hybrid.

*Flower*

Blooming habit:

Location where observations were made—trial field of Michael H. Horvath, Mentor, Ohio.

Recurrent—perpetual.

Bud:

*Size.*—Medium.

*Form.*—Ovoid.

*Color.*—When sepals first divide—dark pink. When petals begin to unfurl—cherry red. When half blown—luminous pink.

*Sepals.*—Smooth.

*Calyx.*—Shape—rounded. Size—medium with small needles. Aspect—smooth. Odor when rubbed—Briar scented.

*Peduncle.*—Length—two to two and a half inches. Aspect—smooth with small needles. Color—glaucous green. Strength—medium.

*Opening.*—Opens well under all weather conditions.

Bloom:

*Size.*—Medium.

*Borne.*—Single and in threes.

*Stems.*—Medium—ample to hold up flower.

*Form.*—When first open—cupped. Permanence—retains form to end.

*Petalage.*—Number of petals under normal conditions—30–36.

*Color.*—Center of flower—cherry red. Outer petals—cherry red. Base of petals—slightly lighter color. Inside of petals—vivid cherry red. Reverse of petals—cherry red. General tonality from a distance—brilliant cherry red accentuated by the orange center.

*Variegations.*—None.

*Discoloration.*—General tonality at end of first and second days—retains color to end. Third day—same.

Petals:

*Texture.*—Moderately thick, unaffected by heat.

*Form.*—Cupped.

*Arrangement.*—Imbricated.

*Petaloids in center.*—None.

*Persistence.*—Drop cleanly.

*Fragrance.*—Damascena-like.

*Nature.*—Hybrid-Thea-like.

*Lasting quality.*—On the plant and as cut flower—last well on plant or cut.

Genital organs:

*Stamens.*—Medium anthers—color—orange.

*Arrangement.*—Regular.

*Stamens, filaments (threads).*—Medium. Color—white.

*Pollen.*—Orange.

*Styles.*—Regular.

*Stigmas.*—White.

*Ovaries.*—None.

Fruit:

*Variety.*—None.

*Plant*

Form: Bush.

Growth: Moderate.

Foliage: Glaucous green.

*Size.*—Medium.

*Quantity.*—Medium.

*Color.*—New foliage—upper side, light green. Under side—reddish green. Old foliage—glaucous green.

*Shape.*—Ovoid—pointed.

*Texture.*—Upper side—glossy. Under side—dull. Ribs and veins—slightly marked.

*Edge.*—Fine, serrated.

*Serration.*—Regular.

*Rachis.* — Clothed. Color — glaucous green. Under side—glaucous green.

*Stipules.*—Smooth above—clothed with small needles.

*Disease resistance.*—Resistant.

Wood:

*New wood.*—Color—reddish green. Bark—reddish green.

*Old wood.*—Color—green—glaucous. Bark—smooth—glaucous green.

Thorns (Thorns are divided into thorns, prickles and short needles):

*Thorns—quantity.*—On main stalks from base—irregular. On laterals from stalk—irregular.

*Form.*—Irregular with wide base, downward hooked.

*Color when young.*—Reddish.

*Position.*—Irregular.

*Prickles.*—Numerous unevenly distributed.

*Short needles.*—None.

Having now fully shown and described my new rose, and the mode of its production, what I claim and desire to secure by Letters Patent of the United States, is:

A rose as herein shown and described and distinguished by the hardiness of the variety, its shrub growth, healthy foliage of a glaucous green color, perpetual flowering, and the vividly brilliant flowers of a glowing red color with a light orange-colored center.

MICHAEL H. HORVATH.